United States Patent
Dorff et al.

(10) Patent No.: US 7,982,038 B2
(45) Date of Patent: *Jul. 19, 2011

(54) LIGANDS

(75) Inventors: Peter Dorff, Wilmington, DE (US); John Gordon, Wilmington, DE (US); John Richard Heys, Wilmington, DE (US); Richard A Keith, Wilmington, DE (US); Dennis J McCarthy, Wilmington, DE (US); Mark A Smith, Wilmington, DE (US); Eifion Phillips, Bothwyn, PA (US)

(73) Assignee: AstraZeneca AB (SE)

( * ) Notice: Subject to any disclaimer, the term of this patent is extended or adjusted under 35 U.S.C. 154(b) by 1222 days.

This patent is subject to a terminal disclaimer.

(21) Appl. No.: 10/573,133

(22) PCT Filed: Sep. 24, 2004

(86) PCT No.: PCT/GB2004/004116
§ 371 (c)(1),
(2), (4) Date: Jan. 12, 2007

(87) PCT Pub. No.: WO2005/030778
PCT Pub. Date: Apr. 7, 2005

(65) Prior Publication Data
US 2007/0172420 A1    Jul. 26, 2007

Related U.S. Application Data

(60) Provisional application No. 60/505,731, filed on Sep. 25, 2003.

(51) Int. Cl.
*C07D 413/04* (2006.01)
*A61K 31/44* (2006.01)

(52) U.S. Cl. ............ 546/18; 514/278; 514/281
(58) Field of Classification Search ............ 546/18; 514/278, 281
See application file for complete search history.

(56) References Cited

U.S. PATENT DOCUMENTS

| 5,726,189 | A | 3/1998 | London et al. | |
|---|---|---|---|---|
| 7,238,715 | B2 * | 7/2007 | Tracey et al. | 514/334 |
| 2004/0157878 | A1 * | 8/2004 | Rogers et al. | 514/303 |

FOREIGN PATENT DOCUMENTS

| EP | 1 213 291 A1 | 6/2002 |
|---|---|---|
| WO | WO 03/087104 A1 | 10/2003 |
| WO | WO 2005/000250 A2 | 1/2005 |

* cited by examiner

*Primary Examiner* — Rita Desai
(74) *Attorney, Agent, or Firm* — Connolly Bove Lodge & Hutz, LLP

(57) ABSTRACT

A radioactive compound having the formula:

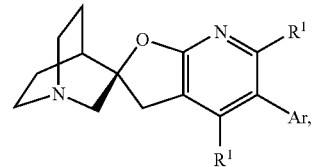

and pharmaceutically-acceptable salts thereof, wherein $R^1$ and Ar are as defined in the specification, enantiomers, in vivo-hydrolysable precursors, pharmaceutical compositions and formulations containing them, methods of using them to treat diseases and conditions either alone or in combination with other therapeutically-active compounds or substances, processes and intermediates used to prepare them and uses of them for diagnostic and analytic purposes.

3 Claims, No Drawings

LIGANDS

RELATED APPLICATIONS

This is a National Phase Application of PCT/GB2004/004116, filed Aug. 24, 2004, which claims the priority of U.S. Provisional Application 60/505,731 filed Sep. 25, 2003.

TECHNICAL FIELD

This invention relates generally to the fields of biochemistry and medicine. More particularly, the present invention relates to isotope-labeled and radio-labeled compounds that bind to nicotinic receptors and their use in discovery of therapeutic compounds, diagnosis, and imaging in neurodegenerative, psychiatric and neurological diseases. The invention also relates to positron emission tomography ligands for nicotinic acetylcholine receptors.

BACKGROUND OF THE INVENTION

Nicotinic acetylcholine receptors are involved in a range of disorders involving reduced cholinergic function such as Alzheimer's disease, cognitive or attention disorders, anxiety, depression, smoking cessation, neuroprotection, schizophrenia, analgesia, Tourette's syndrome, and Parkinson's disease as is discussed in: McDonald et al., (1995) "Nicotinic Acetylcholine Receptors: Molecular Biology, Chemistry and Pharmacology", Chapter 5 in Annual Reports in Medicinal Chemistry, vol. 30, pp. 41-50, Academic Press Inc., San Diego, Calif.; Williams et al., (1994) "Neuronal Nicotinic Acetylcholine Receptors," Drug News & Perspectives, vol. 7, pp. 205-223, and Holladay et al., (1997) *J. Med. Chem.* 40(26), 4169-4194; Arneric and Brioni (Eds.) (1998) "Neuronal Nicotinic Receptors: Pharmacology and Therapeutic Opportunities", John Wiley & Sons, New York; Levin (Ed.) (2001) "Nicotinic Receptors in the Nervous System" CRC Press.

Radio-labeled compounds that bind selectively to a receptor are useful because sensitive and quantitative techniques are available for the detection of the radioactivity which allow the interaction of a compound with its receptor to be detected and measured.

One method of discovering compounds which bind to a receptor is to perform a binding assay where the degree of displacement of a radio-labeled compound by another compound is measured. Thus, radio-labeled forms of compounds that potently bind receptors are useful to screen for novel medicinal compounds which bind to receptors. Such novel medicinal compounds may modulate the activity of those receptors by agonism, partial-agonism, or antagonism.

The ability of analogue compounds to bind to localized receptors within the body makes it possible to utilize such compounds for in situ imaging by PET, SPECT and similar imaging methods. PET imaging is accomplished with the aid of tracer compounds labeled with a positron-emitting isotope: Goodman, M. M. Clinical Positron Emission Tomography, Mosby Yearbook, 1992, K. F. Hubner et al., Chapter 14. For most biological targets, few isotopes are suitable. The carbon isotope, $^{11}C$, has been used for PET, but its short half-life of 20.5 minutes limits its usefulness to compounds that can be synthesized and purified quickly, and to facilities that are proximate to a cyclotron where the precursor $^{11}C$ starting material is generated. Other more energetic isotopes have even shorter half-lives, $^{13}N$ has a half-life of 10 minutes and $^{15}O$ has a half-life of two minutes. Nevertheless, PET studies have been carried out with these isotopes as described by Hubner, K. F., in Clinical Positron Emission Tomography, Mosby Year Book, 1992, K F. Hubner, et al., Chapter 2. [$^{18}F$]-labeled compounds have been used in PET studies, but their use is limited by the 110-minute half-life of the isotope. Most notably, [$^{18}F$]-fluorodeoxyglucose has been widely used in studies of glucose metabolism and localization of glucose uptake associated with brain activity. [$^{18}F$]-L-fluorodopa and other dopamine receptor analogs have also been used in mapping dopamine receptor distribution.

SPECT imaging employs isotope tracers that emit high energy photons (γ-emitters). The range of useful isotopes is greater than for PET, but SPECT provides lower three-dimensional resolution. Nevertheless, SPECT is widely used to obtain clinically significant information about analogue binding, localization and clearance rates. A isotope used for SPECT imaging is $^{123}I$, a γ-emitter with a 13.3 hour half life. Compounds labeled with $^{123}I$ can be shipped up to about 1000 miles from the manufacturing site, or the isotope itself can be transported for on-site synthesis. Eighty-five percent of the isotope's emissions are 159 KeV photons, which is readily measured by SPECT instrumentation currently in use.

Increasingly, the precise location and distribution of receptors in the brain and other tissues is of interest to clinical researchers, clinicians and diagnosticians. The distribution of nAChR's in the brains of individuals having disorders involving reduced cholinergic function such as Alzheimer's disease, cognitive or attention disorders, anxiety, depression, smoking cessation, neuroprotection, schizophrenia, analgesia, Tourette's syndrome, and Parkinson's disease is of growing interest as the molecular bases of these conditions is being discovered. The precise location and distribution of nAChRs in the brain and other tissues is also of importance in assessing the relevance of animal models of these conditions.

DESCRIPTION OF THE INVENTION

In one embodiment, the present invention encompasses nicotinic receptor radio-ligands of formula I:

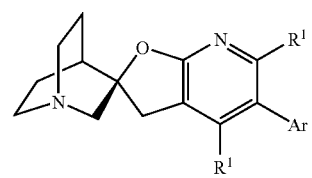

I wherein:
Ar is a moiety formula II:

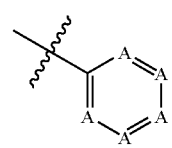

II wherein:
A is independently at each occurrence $CR^1$ or N;
$R^1$ independently at each occurrence is H, $C_1$-$C_6$alkyl, or halogen, provided that at least one occurrence of $R^1$ comprises tritium or a halogen radioisotope.

Other embodiments of the invention encompass enantiomers and pharmaceutically-acceptable salts of the radio-ligands, pharmaceutical compositions and formulations containing them, processes and intermediates used to prepare them and uses of them for diagnostic and analytic purposes.

Compounds of the invention are radio-ligands for nicotinic acetylcholine receptors (nAChRa). Such compounds are compounds of formula I:

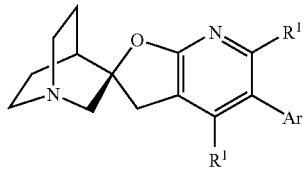

I wherein:
Ar is a moiety formula II:

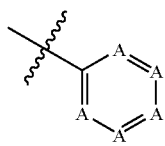

II wherein:
A is independently at each occurrence $CR^1$ or N;
$R^1$ is independently at each occurrence H, $C_1$-$C_6$alkyl, or halogen, provided that at least one occurrence of $R^1$ comprises tritium or a halogen radioisotope.

Certain embodiments of the invention are those in which no more than one occurrence of A is nitrogen.

Other embodiments of the invention are those in which no more than two occurrences of $R^1$ are other than hydrogen.

A particular aspect of the invention are compounds in which Ar is a moiety of formula III.

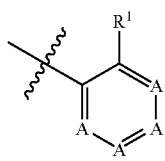

III

Particular embodiments of this aspect of the invention are compounds wherein $R^1$ is hydrogen or fluorine, and A is N at no more than one occurrence.

More particular embodiments of this aspect of the invention are those in which Ar is selected from phenyl, 2-[$^{18}$F]fluorophenyl or 2-[$^{18}$F]fluoro-3-pyridyl.

Particular embodiments of the invention are also those in which the radioisotope is tritium.

Other particular embodiments of the invention are those in which the radioisotope is selected from $^{18}$F, $^{123}$I, $^{125}$I, $^{124}$I, $^{131}$I, $^{75}$Br, $^{76}$Br, $^{77}$Br or $^{82}$Br.

Most particular embodiments of the invention are those in which the radioisotope is $^{18}$F.

Particular embodiments of the invention are compounds of formulae IV, V, VI, VII, VIII and IX:

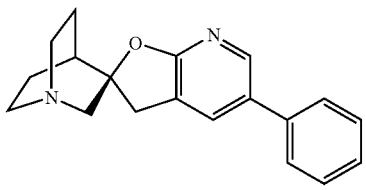

(IV)

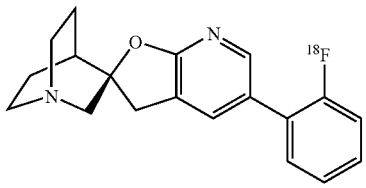

(V)

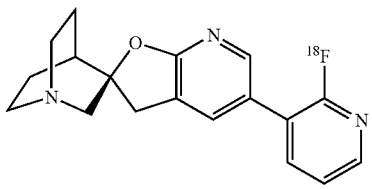

(VI)

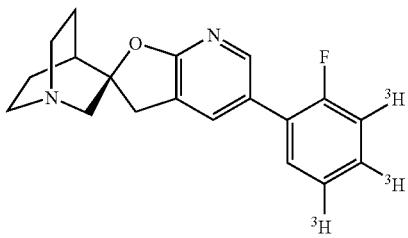

(VII)

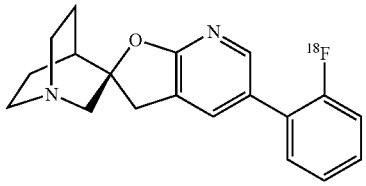

(VIII)

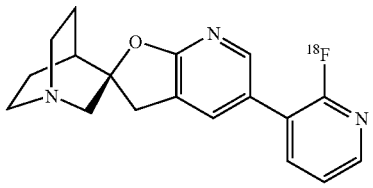

(IX)

Another aspect of the invention relates to a diagnostic composition comprising a compound of the invention, and a pharmaceutically-acceptable diluent or carrier.

Another aspect of the invention relates to the use of a diagnostic composition for the diagnosis of human diseases or conditions in which detection of the α7 nicotinic receptor beneficial.

Another aspect of the invention relates to the use of a diagnostic composition for the diagnosis of psychotic disorders or intellectual impairment disorders.

Another aspect of the invention relates to use of a diagnostic composition for the diagnosis of Alzheimer's disease, learning deficit, cognition deficit, attention deficit, memory loss, Attention Deficit Hyperactivity Disorder, anxiety, schizophrenia, mania, manic depression, Parkinson's disease, Huntington's disease, Tourette's syndrome, neurodegenerative disorders in which there is loss of cholinergic synapse, jetlag, cessation of smoking, nicotine addiction including that resulting from exposure to products containing nicotine, craving, pain, and for ulcerative colitis.

A further aspect of the invention is method for diagnosis of diseases or conditions in which detection of the α7 nicotinic receptor beneficial. Such a method comprises administering to a subject a detectable amount of a compound of the invention, detecting the presence and distribution of said compound in the subject, analyzing the distribution of the compound in the subject and using the determined distribution to assess the disease or condition of the subject.

In a particular embodiment of this aspect of the invention the method is used for the diagnosis of psychotic disorders or intellectual impairment disorders.

In another embodiment of this aspect of the invention the method is used for the diagnosis of Alzheimer's disease, learning deficit, cognition deficit, attention deficit, memory loss, Attention Deficit Hyperactivity Disorder, anxiety, schizophrenia, mania, manic depression, Parkinson's disease, Huntington's disease, Tourette's syndrome, neurodegenerative disorders in which there is loss of cholinergic synapse, pain, and for ulcerative colitis.

Another aspect of the invention relates to a use of a compound as described above in the manufacture of a diagnostic agent for use in the diagnosis of human diseases or conditions in which activation of the α7 nicotinic receptor is beneficial.

A further aspect of the invention is a kit useful for diagnosis of diseases and conditions mentioned herein. Such a kit includes a detectable quantity of a compound of the invention in administrable form and instructions for administering the compound and thereafter detecting the distribution of the compound in a subject.

Methods of Preparation

A particularly useful isotope, $^{18}F$, has a half-life of 110 minutes. Thus, $^{18}F$ may be incorporated into a radio-labeled compound, the compound purified and administered to a human or animal subject. In addition, facilities up to about a 200 mile from a cyclotron can make use of $^{18}F$ labeled compounds. However, relatively few fluorinated analogs that have functional equivalence to naturally-occurring biological materials are known, and few methods of synthesis efficiently utilize the starting material generated in the cyclotron. Such starting material can be either fluoride ion or fluorine gas. In the latter case usually only one fluorine atom of the bimolecular gas is a radionuclide, so the gas is designated $^{18}F-F$. Reactions using 18F—F as starting material therefore yield products having no more than one half the radionuclide abundance of reactions utilizing $K^{18}F$ as a starting material. However, $^{18}F$ can be prepared in curie quantities as fluoride ion for incorporation into a compound to yield a high specific activity, theoretically 1.7 Ci/nmol using carrier-free nucleophilic substitution reactions. The energy emission of $[^{18}F]$ (0.635 MeV) is also advantageous, resulting in a relatively short, 2.4 mm average positron range in tissue, permitting high resolution PET images.

Other halogen isotopes are useful for PET or SPECT imaging, and for conventional tracer labeling. These include $^{75}Br$, $^{76}Br$, $^{77}Br$, $^{82}Br$, $^{123}I$, $^{124}I$, $^{125}I$ and $^{131}I$ which have usable half-lives and emission characteristics. In general, chemical strategies exist that permit substitution of any of the described isotopes for halogen moiety. Therefore, the biochemical or physiological activities of any halogenated homologue of the described compounds are now available for use by those skilled in the art, including stable isotope halogen homologues.

Astatine can also be substituted for other halogen isotopes. $^{210}At$ has a half life of 8.3 hours and emits alpha particles. At-substituted compounds are therefore useful for tumor therapy, provided binding is sufficiently tumor-specific.

Methods which may be used for the synthesis of compounds of formula I include the method outlined in herein. Unless otherwise noted Ar and $R^1$ are as defined herein for Formula 1.

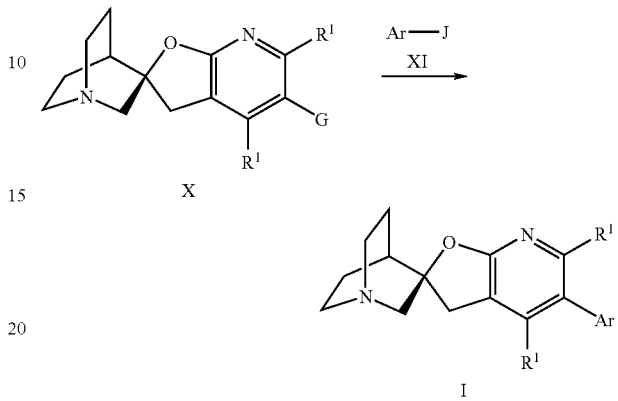

Scheme 1

The compounds of formula I may be prepared by the cross-coupling reaction of compounds of formula X and XI, wherein either G or J is halogen or $OSO_2CF_3$ when, respectively, J or G is an organometallic group. Suitable organometallic groups include boronic acid or boronic ester groups, $B(OH)_2$, $B(OR)_2$, or a trialkylstannyl group $SnR_3$, wherein R is an alkyl group. The reaction is performed in the presence of a suitable organometallic catalyst and solvent. Suitable organometallic catalysts include palladium (0) complexes, for example tetrakis(triphenylphosphine)palladium(0) or a combination of tris(dibenzylideneacetone)dipalladium(0) and a suitable triarylphosphine or triarylarsine ligand, for example triphenylphosphine, tri(o-tolyl)phosphine or triphenylarsine. Suitable solvents include inert ether solvents, for example 1,2-dimethoxyethane, tetrahydrofuran, or 1,4-dioxane, or alcohols, such as ethanol, or mixtures thereof. If the compound of formula X or XI is a boronic acid, the presence of a suitable base in addition to the other reagents is preferred. Suitable bases include sodium carbonate, cesium carbonate, and barium hydroxide. The reaction is carried out at a temperature of 0-120° C., and preferably at a temperature of 60-120° C.

Compounds of formula X wherein G or J is an organometallic group or compounds of formula XI, wherein either J of G respectively is an organometallic group may be prepared from compounds of the corresponding formula wherein G or J is hydrogen, halogen, or $OSO_2CF_3$ by a suitable metallation or exchange procedure. The compounds wherein the organometallic group is $B(OH)_2$ may be prepared from suitable aromatic compounds having hydrogen or halogen groups, by conversion to the corresponding aryllithium or arylmagnesium compounds followed by reaction with trialkylborate and subsequent hydrolysis of the resulting borate ester. Similarly, compounds wherein the organometallic group is a trialkylstannyl group may be prepared from suitable aromatic compounds having hydrogen or halogen groups, by conversion to the corresponding aryllithium or arylmagnesium compounds followed by reaction with an appropriate trialkylstannyl halide. The formation of the aryllithium or arylmagnesium compound is performed in a suitable inert solvent, for example, tetrahydrofuran. Alternatively, the compounds wherein the organometallic group is $B(OH)_2$ may be prepared from suitable aromatic compounds having halogen or $OSO_2CF_3$ groups by reaction with bis(pinacolato)diboron and an organometallic catalyst, followed by hydrolysis of the resulting borate ester, compounds wherein the said organometallic group is a trialkylstannyl group may be prepared from suitable aromatic compounds having halogen or $OSO_2CF_3$ groups by reaction with the appropriate bis(trialkyltin) in the presence of a suitable organometallic catalyst. The reaction is performed in a suitable inert solvent, for example tetrahydrofuran, and suitable organometallic catalyst include, for example tetrakis(triphenylphosphine)palladium(0). The reaction is performed at a temperature of about 0° C. to about 150° C., preferably about 20° C. to about 100° C. Typical procedures for effecting such conversions will be known to those of skill in the art.

The synthesis of radioactive compounds of formula I may be prepared by employing suitable radioactive starting materials in the above-described procedures, whereby a group $R^1$ in one of the starting materials is the radioisotope which it is desired to incorporate into the compound of formula I. Such starting materials are synthesized by methods known to one skilled in the art of organic chemical synthesis, and radiochemical synthesis. The initial introduction of the radioisotope into a starting material would most usually be by an aromatic substitution reaction or functional group transformation reaction employing a suitable radioactive reagent. For the compounds of the invention, wherein the radioisotope is tritium, or a radioisotope of a halogen, suitable radioactive reagents for the initial introduction of the radioisotope, would include tritium gas, or the radioactive elemental halogen or metal halide. Specific examples of procedures which may be employed for the introduction of tritium include catalytic reduction of an aromatic halide, whereby one or more halogen substitutents in a precursor is reduced with tritium gas in the presence of a transition metal catalyst, or an exchange procedure whereby hydrogen is exchanged for tritium by treatment with tritium gas in the presence of an organometallic catalyst. Specific examples of procedures which may be used for the introduction of a halogen radioisotope include by halogenation with a suitable source of the radioactive electrophilic halogen. Particularly useful for the introduction of radioactive bromide or iodide is when the electrophilic substitution reaction is performed upon an aryltrialkylstannyl precursor, treatment a suitable electrophilic source of the radioactive halogen converting the arylstannyl group to an aryl halide. Another method that is useful is replacement of a leaving group in a nucleophilic substitution reaction with a suitable radioactive metal halide. This procedure is particularly useful for the introduction of $^{18}F$, through the nucleophilic substitution of suitable leaving groups with $^{18}F$-fluoride.

In radiosynthesis, it is preferable if the reaction which introduces the radioisotope is performed as late as possible in the synthetic sequence, most preferably as the last step. Thus a particularly useful method for synthesis of the radioactive compounds of the invention is that illustrated in Scheme 2 below, in which the introduction of the radioisotope is performed as the last step of the synthesis:

Scheme 2

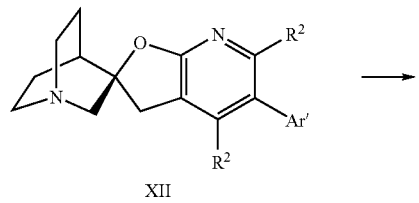

XII

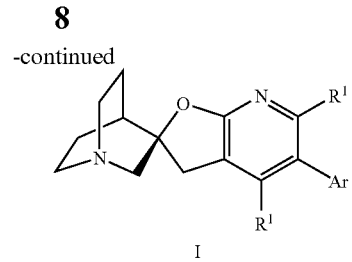

I wherein:
Ar' is a moiety of formula XIII:

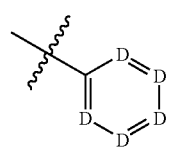

XIII wherein:
D is independently at each is occurrence $CR^2$ or N;
provided $R^2$ independently at each occurrence is either $R^1$, or is a precursor group selected from halogen or trialkylstannyl that, in the transformation depicted Scheme 2 becomes an occurrence of $R^1$ in formula I which is a radioisotope of either hydrogen or a halogen.

The intermediates of formula XII and the processes for transforming compounds of formula XII to compounds of formula I are yet further aspects of the invention. Particular embodiments of this aspect of the invention are described below.

(1) $R^2$=Halogen Transformed to $R^1=^3H$

One or more occurrences of $R^2$ in formula XII is halogen, preferably bromine or iodine, and is transformed to a compound of formula I wherein the corresponding occurrence of $R^1$ is tritium by a process comprising treatment of the compound of formula XII with tritium gas in the presence of a transition metal catalyst. Suitable transition metal catalysts include palladium, platinum, rhodium, which may be in the form of the element, including as metal blacks, oxides, hydroxides, and on various supports.

In a particular embodiment of this aspect of the invention the compound of formula XII is:
(2'R)-5'-(3,4,5-tribromo-2-fluorophenyl)spiro[1-azabicyclo[2.2.2]octane-3,2'(3'H)-furo[2,3-b]pyridine] having the following formula

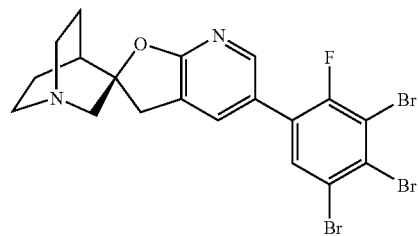

(2) $R^2$=trialylstannyl Transformed to $R^1$=halogen

One or more occurrences of $R^2$ in formula XII is a trialkylstannyl group, for example a trimethylstannyl group or a tributylstannyl group, and is transformed to a compound of formula I wherein the corresponding occurrence of $R^1$ is halogen by a process comprising treatment of the compound of formula XII with an electrophilic form of a halogen radioisotope. Suitable electrophilic forms of the halogen include the elemental halogen, the N-halosuccinimide, or a metal halide converted to electrophilic form by reaction with an oxidizing agent.

(3) $R^2$=a Suitable Leaving Group Transformed to $R^1$=$^{18}$F

One occurrence of $R^2$ in formula XII is a suitable leaving group such as diazonium, trialkylammonium, nitro, or halogen, and is transformed to a compound of formula I wherein the corresponding occurrence of $R^1$ is $^{18}$F by a process comprising treatment of the compound of formula XII with $^{18}$F-fluoride. The process is preferably performed at an elevated temperature, preferably greater than 100° C. in a polar solvent, for example dimethyl sulfoxide or dimethyl sulfone.

Pharmacology

The suitability of the compounds as radio-ligands may be assessed by determining the binding potency of the compounds in non-radiolabeled form by a competition binding assay whereby the affinity of the compound relative to that of the known nicotinic ligand [$^{125}$I]-α-bungarotoxin (BTX) is measured.

Test A—Assay for Affinity at α7 nAChR Subtype

[$^{125}$I]-α-Bungarotoxin (BTX) binding to rat hippocampal membranes. Rat hippocampi were homogenized in 20 volumes of cold homogenization buffer (HB: concentrations of constituents (mM): tris(hydroxymethyl)aminomethane 50; $MgCl_2$ 1; NaCl 120; KCl 5: pH 7.4). The homogenate was centrifuged for 5 minutes at 1000 g, the supernatant was saved and the pellet re-extracted. The pooled supernatants were centrifuged for 20 minutes at 12000 g, washed, and resuspended in HB. Membranes (30-80 µg) were incubated with 5 nM [$^{125}$I]-α-BTX, 1 mg/mL BSA (bovine serum albumin), test drug, and either 2 mM $CaCl_2$ or 0.5 mM EGTA [ethylene glycol-bis(β-aminoethylether)] for 2 hours at 21° C., and then filtered and washed 4 times over Whatman glass fibre filters (thickness C) using a Brandel cell harvester. Pretreating the filters for 3 hours with 1% (BSA/0.01% PEI (polyethyleneimine) in water was critical for low filter blanks (0.07% of total counts per minute). Nonspecific binding was described by 100 µM (−)-nicotine, and specific binding was typically 75%.

Test B—Assay for Affinity to the α4 nAChR Subtype

[$^3$H]-(−)-nicotine binding. Using a procedure modified from Martino-Barrows and Kellar (Mol Pharm (1987) 31:169-174), rat brain (cortex and hippocampus) was homogenized as in the [$^{125}$I]α-BTX binding assay, centrifuged for 20 minutes at 12,000×g, washed twice, and then resuspended in HB containing 100 µM diisopropyl fluorophosphate. After 20 minutes at 4° C., membranes (approximately 0.5 mg) were incubated with 3 nM [$^3$H]-(−)-nicotine, test drug, 1 µM atropine, and either 2 mM $CaCl_2$ or 0.5 mM EGTA for 1 h at 4° C., and then filtered over Whatman glass fibre filters (thickness C) (pretreated for 1 h with 0.5% PEI) using a Brandel cell harvester. Nonspecific binding was described by 100 µM carbachol, and specific binding was typically 84%.

Binding Data Analysis for Tests A and B $IC_{50}$ values and pseudo Hill coefficients (nH) were calculated using the non-linear curve-fitting program ALLFIT (DeLean A, Munson P J and Rodbard D (1977) Am. J. Physiol., 235:E97-E102). Saturation curves were fitted to a one site model, using the non-linear regression program ENZFITTER (Leatherbarrow, R. J. (1987)), yielding KD values of 1.67 and 1.70 nM for the $^{125}$I-α-BTX and [3H]-(−)-nicotine ligands respectively. Ki values were estimated using the general Cheng-Prusoff equation:

$$Ki=[IC_{50}]/((2+([ligand]/[KD])n)1/n−1)$$

where a value of n=1 was used whenever nH<1.5 and a value of n=2 was used when nH≧1.5. Samples were assayed in triplicate and were typically ±5%. Ki values were determined using 6 or more drug concentrations. The compounds of the invention are compounds with binding affinities (Ki) of less than 1000 nM in either Test A or Test B, indicating that they are expected to have useful therapeutic activity.

EXAMPLES

Intermediate 1: (2'R)-5'-Trimethylstannylspiro[1-azabicyclo[2.2.2]octane-3,2'(3'H)-furo[2,3-b]pyridine]

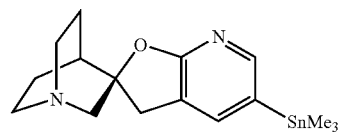

(2'R)-5'-Bromospiro[1-azabicyclo[2.2.2]octane-3,2'(3'H)-furo[2,3-b]pyridine] (690 mg, 2.34 mmol) (prepared as described in U.S. Pat. No. 6,110,914 the disclosure of which is incorporated herein by reference) hexamethylditin (1.225 g, 0.27 mmol) and tetrakis(triphenylphosphine)palladium(0) (266 mg, 0.027 mmol) were mixed with 10 mL of toluene and sealed under nitrogen. The mixture was stirred and heated at 120° C. under nitrogen for 4 h. The mixture was allowed to cool, then filtered through diatomaceous earth. The filtrate was diluted with chloroform, washed with saturated sodium bicarbonate, dried through $MgSO_4$, filtered, and then the solvent was evaporated. The residue was purified by flash chromatography using a gradient of ammoniated methanol in chloroform to give the title compound as a pale solid; m/z 377 379 381 (M+).

Example 1

(2'R)-5'-(2-fluorophenyl)spiro[1-azabicyclo[2.2.2]octane-3,2'(3'H)-furo[2,3-b]pyridine

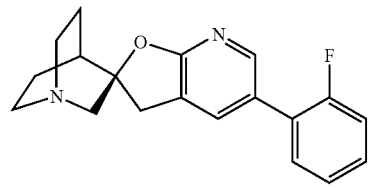

A solution of (2'R)-5'-trimethylstannylspiro[1-azabicyclo[2.2.2]octane-3,2'(3'H)-furo[2,3-b]pyridine] (190 mg, 0.50 mmol) in dry toluene (5 mL) was treated with 2-bromofluorobenzene (88 mg, 0.50 mmol) and tetrakis(triphenylphosphine)palladium(0) (58 mg, 0.05 mmol). The resulting solution was heated at 110° C. under a nitrogen atmosphere for 45 min. The reaction was sampled at t=0 min and t=30 min and analyzed by LC/MS. The reaction was essentially complete at t=30 min. The reaction was allowed to cool to room temperature and filtered through diatomaceous earth. The filter cake was washed with 10 mL of chloroform and the combined filtrate/washing was concentrated on a rotary evaporator. The residue was purified by preparative HPLC (Waters $C_{18}$ column, eluting with 0 to 80% acetonitrile in water buffered with 0.1% v/v trifluoroacetic acid, over 20 minutes) to give 68 mg of the title compound as a colorless oil.

Example 2

(2'R)-5'-(4-Amino-2-fluorophenyl)spiro[1-azabicyclo[2.2.2]octane-3,2'(3'H)-furo[2,3-b]pyridine

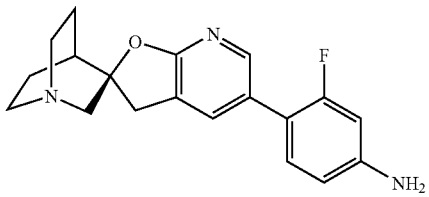

To a 5 mL volume of dry toluene under an atmosphere of nitrogen in a 25 mL flask with stirring bar was added in succession (2'R)-5'-trimethylstannylspiro[1-azabicyclo[2.2.2]octane-3,2'(3'H)-furo[2,3-b]pyridine] (181 mg, 0.478 mmol), tetrakis(triphenylphosphine)palladium(0) (52 mg, 0.045 mmol) and 4-bromo-3-fluoroaniline (91 mg, 0.478 mmol). The mixture was heated with stirring to 120° C. for 21 h, then allowed to cool to ambient temperature. The reaction mixture was treated with 10 mL of chloroform, stirred 5 min. then filtered through a bed of diatomaceous earth. The filtrate was evaporated to dryness, the glassy residue was dissolved in 6 mL of 3:2 acetonitrile/water, then purified by HPLC on a $C_{18}$ column eluting with an acetonitrile/water gradient containing 0.1% TFA. Product-containing fractions were combined, the solvents were removed under vacuum, and the gummy residue then triturated with hexane and ether. The residue was treated with 4 mL saturated aqueous $NaHCO_3$, then the mixture was extracted with chloroform (3×5 mL). The combined extracts were dried over $MgSO_4$, filtered, and evaporated to give 31 mg of the product as a colorless solid (12271-103-A). NMR (DMSO-$d_6$): δ 7.926 (s, 1H), 7.609 (s, 1H), 7.110 (t, 1H, J=8.7 Hz), 6.429 (s, 1H), 6.420 (dd, 1H, J=23 Hz, 0.5 Hz), 3.440 (d, 1H, J=16.5 Hz), 3.269 (s, 1H), 3.103 (d, 1H, J=16.8 Hz), 3.057 (d, 1H, J=13.8 Hz), 2.951 (d, 1H, J=14.4 Hz), 2.792 (t, 2H, J=8.4 Hz), 2.685 (t, 2H, J=7.8 Hz), 1.94 (m, 2H), 1.60 (m, 2H).

Example 3

(2'R)-5'-(3,4,5-Tribromo-2-fluorophenyl)spiro[1-azabicyclo[2.2.2]octane-3,2'(3'H)-furo[2,3-b]pyridine

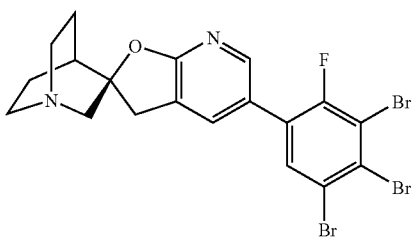

To a suspension of (2'R)-5'-(4-amino-2-fluorophenyl)spiro[1-azabicyclo[2.2.]octane-3,2'(3'H)-furo[2,3-b]pyridine (30 mg, 0.092 mmol) stirred in acetonitrile (0.5 mL) in a vial with magnetic stirrer was added $CuBr_2$ (4 mg, 0.018 mmol), followed by bromine (19 μL, 0.368 mmol) were added, and the loosely capped vial was heated with stirring at 50° C. for 45 min. After this time t-butyl nitrite (13 μL, 0.11 mmol) of was added, which caused immediate bubbling. After stirring for an additional 30 min at 50° C., the mixture was cooled to ambient temperature then diluted with 10% aqueous $Na_2SO_3$ (about 200 μL), and the dark brown reaction mixture changed color to yellow. The mixture was diluted with water then extracted with chloroform (2×3 mL). The combined extracts were washed with dilute aqueous $Na_2CO_3$ then dried over $MgSO_4$. The mixture was filtered and the filtrate evaporated to dryness to yield (2'R)-5'-(3,4,5-tribromo-2-fluorophenyl)spiro[1-azabicyclo[2.2.2]octane-3,2'(3'H)-furo[2,3-b]pyridine (43 mg) as a yellow glassy solid. NMR (DMSO-$d_6$): δ 8.127 (s, 1H), 7.988 (d, 1H, $J_{FH}$=7.5 Hz), 7.820 (s, 1H), 3.482 (d, 1H, J=17.0 Hz), 3.271 (s, 1H), 3.154 (d, 1H, J=17.6 Hz), 3.097 (d, 1H, J=16.4 Hz), 2.984 (d, 1H, J=15.1 Hz), 2.807 (t, 2H, J=7.9 Hz), 2.701 (t, 2H, J=7.6 Hz), 1.97 (m, 2H), 1.60 (m, 2H). MS: $[M+H]^+$ m/z 545 (30%), 547 (100%), 549 (80%), 551 (20%).

Example 4A

Deuterium-labeled (2'R)-5'-(2-fluorophenyl)spiro[1-azabicyclo[2.2.2]octane-3,2'(3'H)-furo[2,3-b]pyridine

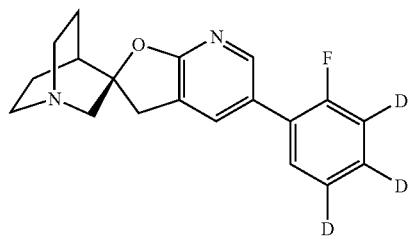

Palladium (5% on carbon, 4 mg) was placed in a 10 mL flask with magnetic stirring bar. An atmosphere of deuterium gas was established in the flask, then a solution of 4 mg of (2'R)-5'-(3,4,5-tribromo-2-fluorophenyl)spiro[1-azabicyclo[2.2.2]octane-3,2'(3'H)-furo[2,3-b]pyridine in 1 mL of 95% ethanol and 50 μL of triethylamine was added. The mixture was stirred vigorously under $D_2$ for 85 min then worked up by evaporating the solvent under reduced pressure, suspending the residue in chloroform, filtering it through a layer of diatomaceous earth and evaporating the filtrate to provide 1.8 mg of the deuterium labeled compound m/Z 312 (13%), 313 (92%), 314 (100%), 315 (17%), calculated to contain 2.34 moles deuterium/mole.

Example 4B

Tritium-labeled (2'R)-5'-(2-fluorophenyl)spiro[1-azabicyclo[2.2.2]octane-3,2'(3'H)-furo[2,3-b]pyridine

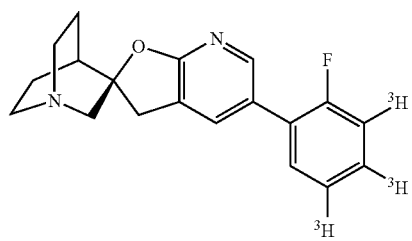

Tritium labeling was performed using a method analogous to that of step (d) above from (2'R)-5'-(3,4,5-tribromo-2-fluorophenyl)spiro[1-azabicyclo[2.2.2]octane-3,2'(3'H)-furo[2,3-b]pyridine compound using tritium gas. Tritium-labeled (2'R)-5'-(2-fluorophenyl)spiro[1-azabicyclo[2.2.2]

octane-3,2'(3'H)-furo[2,3-b]pyridine was obtained at a specific activity of 69 Ci/mmole, equivalent to 2.37 moles tritium/mole.

Example 4C

[$^{18}$F]-labeled (2'R)-5'-(2-fluorophenyl)spiro[1-azabicyclo[2.2.2]octane-3,2'(3'H)-furo[2,3-b]pyridine (a) N,N-Dimethyl-2-bromoaniline

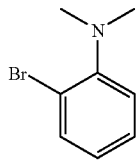

2-Bromoaniline (21.3 g, 124 mmol), and sodium borohydride (27.5 g) were suspended in THF (~100 mL) and the suspension was added portion-wise to a mixture of 37% formalin (35 mL), aqueous sulfuric acid (3 M, 35 mL), and THF (250 mL) which was stirred in a cold water bath. When the addition was approximately 50% complete, further aqueous sulfuric acid (3 M, 35 mL), was added. After the addition was complete the mixture was stirred for a further 1 h, then water was added. The mixture was basified by the addition of solid potassium hydroxide, then was extracted with ether. The ether extract was washed with water and brine, then dried, filtered, and evaporated. The residue was subjected to bulb-to-bulb distillation under reduced pressure to give the title compound as an oil (21.2 g), MS (m/z) 200, 202 (MH$^+$).

(b) 2-Bromophenyltrimethylammonium trifluoromethanesulfonate

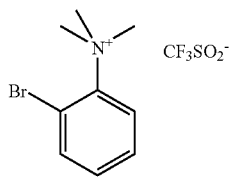

N,N-Dimethyl-2-bromoaniline (2.0 g, 10 mmol) was stirred under inert atmosphere at −78° C. Trifluoromethylsulfonic acid methyl ester (1.5 mL, 2.2 g, 13 mmol) was added, then the mixture was stirred and allowed to warm to room temperature over 2 h. The mixture was then partitioned between hexane and water. The aqueous layer was evaporated, then solvent was added to the residue and then evaporated; this procedure was repeated using successively methanol, methyl t-butyl ether and finally hexane as the solvent. The residue was crystallized from isopropanol/hexane to give the title compound as an oil.

(c) ($^{18}$F]-labeled) (2'R)-5'-(2-fluorophenyl)spiro[1-azabicyclo[2.2.2]octane-3,2'(3H)-furo[2,3-b]pyridine

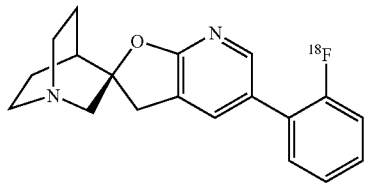

Potassium [$^{18}$F-fluoride is prepared by proton bombardment of $^{18}$O water followed by capture of the fluoride anion on Dowex ion exchange resin and elution with dilute potassium carbonate. The potassium fluoride is heated with 2-bromophenyltrimethylammonium trifluoromethanesulfonate in a suitable aprotic solvent to give 2-bromo-[$^{18}$F]-fluorobenzene. A potassium cation sequestering agent such as 4,7,13,16,21,24-hexaoxa-1,10-diazabicyclo[8.8.8]hexacosane may be beneficial for the successful performance of this reaction. 2-Bromo-[$^{18}$F]-fluorobenzene is then treated with (2'R)-5'-trimethylstannylspiro[1-azabicyclo[2.2.2]octane-3,2'(3'H)-furo[2,3-b]pyridine] under conditions analogous to those described in Example 1, above, adapted to the small scale synthesis of the PET tracer. The compound is purified by reverse phase HPLC.

Example 5

(2'R)—(2-fluorophenyl)spiro[1-azabicyclo[2.2.2]octane-3,2'(3'H)-furo[2,3-b]pyridine (a) (2'R)—(5-formyl-2-nitrophenyl)spiro[1-azabicyclo[2.2.2]octane-3,2' (3'H)-furo[2,3-b]pyridine

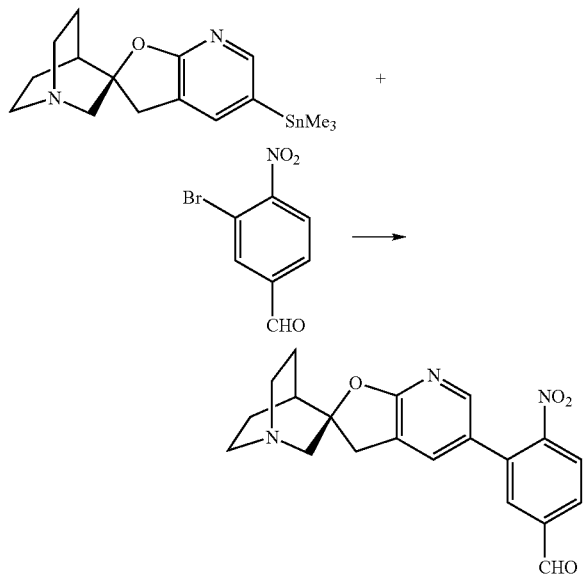

A mixture of 3-bromo-4-nitrobenzaldehyde (247 mg, 1.07 mmol), (2'R)-5'-trimethylstannylspiro[1-azabicyclo[2.2.2]octane-3,2'(3'H)-furo[2,3-b]pyridine (406 mg, 1.07 mmol), and Pd(PPh$_3$)$_4$ (186 mg, 161 µmol) in anhydrous toluene (15 mL) was heated to reflux under argon for 20 h. The mixture was concentrated in vacuo, dissolved in MeOH (10 mL) and filtered through a 0.45 µm filter. The solution was concentrated and redissolved in 1:1 acetonitrile:H$_2$O. The product was isolated by preparative reverse-phase chromatography using a gradient of acetonitrile/water to give the title compound as an orange oil (156 mg, 40%).

(b) (2'R)—(2-fluoro-5-formylphenyl)spiro[1-azabicyclo[2.2.2]octane-3,2'(3'H)-furo[2,3-b)pyridine

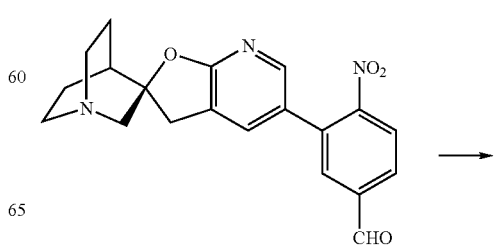

-continued

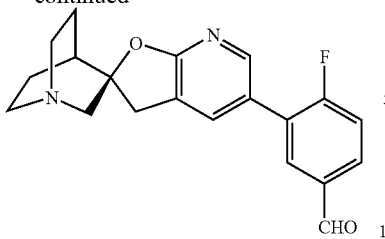

An aqueous potassium fluoride solution (7.5 μL, 4.1 μmol of KF) was transferred into a conical glass vial containing 4,7,13,16,21,24-hexaoxa-1,10-diazabicyclo[8.8.8]hexacosane (5 mg, 13.2 μmol) and $K_2CO_3$ (0.5 mg, 3.62 μmol) in 500 μL of acetonitrile. The water was removed by azeotropic distillation with anhydrous acetonitrile (3×300 μL) at 100° C., under a stream of argon. A 500 μL portion of dry DMSO was added to dissolve the residue. A solution of (2'R)—(5-formyl-2-nitrophenyl)spiro[1-azabicyclo[2.2.2]octane-3,2' (3'H)-furo[2,3-b]pyridine (1.5 mg, 4.1 μmol) in 250 μL of dry DMSO was added to this solution. The vial was sealed with a teflon faced septum and heated at 130° C. The progress of the reaction was monitored by reverse phase LC-MS, and the yield of product was found to reach a maximum (69%) in about 25 min. The reaction mixture was diluted to 5 mL with water and loaded onto a cartridge of $C_{18}$ silica gel (500 mg) preconditioned by washing with methanol then water. The loaded cartridge was washed with 5 mL of water, then the title compound was eluted with 2 mL of MeOH into a 4 mL flat-bottomed glass vial. The methanol was removed by heating the solution at 100° C. under a steam of argon. Any residual water was removed with a further azeotropic distillation using anhydrous acetonitrile (2×300 μL).

(c) (2'R)—(2-fluorophenyl)spiro[1-azabicyclo[2.2.2]octane-3,2' (3'H)-furo[2,3-b]pyridine

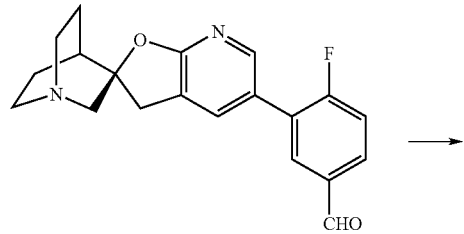

→

-continued

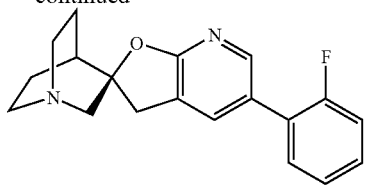

While the vial was still under argon but removed from heat, 200 μL of anhydrous dioxane was added, followed by RhCl(PPh$_3$)$_3$ (6.5 mg, 7.0 μmol). The vial was sealed and heated at 130° C. The progress of the reaction was monitored by reverse phase LC-MS, and the yield of product was found to reach a maximum (66%) within 10 min. Synthesis of the title compound was confirmed by fractionation of the reaction mixture in a suitable HPLC-MS and detection of an eluate having a mass and retention time identical to those of an independently prepared authentic example of the title compound.

The invention claimed is:

1. A compound in accord with formula I:

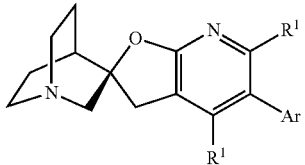

wherein: Ar is 2-[$^{18}$F]fluoro-3-pyridyl wherein:

$R^1$ is independently at each occurrence H, $C_1$-$C_6$alkyl, or halogen.

2. A compound according to claim 1, wherein $R^1$ is hydrogen or fluorine.

3. A diagnostic composition comprising said compound of claim 1 and a pharmaceutically-acceptable diluent or carrier.

\* \* \* \* \*